(12) United States Patent
Chun et al.

(10) Patent No.: US 11,298,534 B2
(45) Date of Patent: Apr. 12, 2022

(54) STIMULATOR FOR DIGESTIVE ORGAN

(71) Applicants: KOREA UNIVERSITY RESEARCH AND BUSINESS FOUNDATION, Seoul (KR); Korea University Research and Business Foundation, Sejong Campus, Sejong-si (KR)

(72) Inventors: Hoon Jai Chun, Seoul (KR); Jung Hwa Hong, Seoul (KR); Dong Geun Sul, Seoul (KR); Bora Keum, Seoul (KR); Eun Sun Kim, Seoul (KR); Hyuk Soon Choi, Seoul (KR); Seung Han Kim, Seoul (KR)

(73) Assignees: KOREA UNIVERSITY RESEARCH AND BUSINESS FOUNDATION, Seoul (KR); KOREA UNIVERSITY RESEARCH AND BUSINESS FOUNDATION, SEJONG CAMPUS, Sejong-si (KR)

( * ) Notice: Subject to any disclaimer, the term of this patent is extended or adjusted under 35 U.S.C. 154(b) by 151 days.

(21) Appl. No.: 16/235,498

(22) Filed: Dec. 28, 2018

(65) Prior Publication Data
US 2019/0321631 A1   Oct. 24, 2019

(30) Foreign Application Priority Data
Apr. 24, 2018   (KR) .................. 10-2018-0047351

(51) Int. Cl.
*A61N 1/00* (2006.01)
*A61N 1/36* (2006.01)
(Continued)

(52) U.S. Cl.
CPC ....... *A61N 1/36007* (2013.01); *A61N 1/0507* (2013.01); *A61N 1/37205* (2013.01);
(Continued)

(58) Field of Classification Search
None
See application file for complete search history.

(56) References Cited

U.S. PATENT DOCUMENTS 8,257,257 B2 * 9/2012 Takizawa ............... A61B 1/041
600/302
8,295,932 B2  10/2012 Bitton et al.
(Continued)

FOREIGN PATENT DOCUMENTS

KR   10-2014-0098780 A   8/2014
KR   10-2017-0046593 A   5/2017
WO   WO-2018111943 A1 *  6/2018 ......... A61N 1/36007

OTHER PUBLICATIONS

Kim, et al., "Minimally Invasive Gastric Stimulation using Newly Developed Wireless Gastrostimulator: A Pilot Study", KDDW 2017—Oral Presentations, Nov. 25, 2017 (26 pages)(This document involves a presentation of the present inventor(s)).
(Continued)

*Primary Examiner* — Gary Jackson
*Assistant Examiner* — Anant A Gupta
(74) *Attorney, Agent, or Firm* — WHDA, LLP

(57) ABSTRACT

A stimulator for a digestive organ includes a case, a substrate member disposed in the case, and an electrode member connected to the substrate member and extending to protrude outwardly from the case. The electrode member may have a shape of a wire and may be configured to provide an electrical stimulation in a state of being inserted and fixed at a predetermined location within a digestive organ.

12 Claims, 4 Drawing Sheets

(51) Int. Cl.
*A61N 1/372* (2006.01)
*A61N 1/05* (2006.01)
A61B 17/00 (2006.01)

(52) U.S. Cl.
CPC ....... *A61B 17/00234* (2013.01); *A61N 1/0517* (2013.01); *A61N 1/37211* (2013.01)

(56) References Cited

U.S. PATENT DOCUMENTS

| | | | |
|---|---|---|---|
| 2004/0138761 A1 | 7/2004 | Stack et al. | |
| 2008/0065169 A1* | 3/2008 | Colliou | A61N 1/05 607/40 |
| 2009/0149910 A1* | 6/2009 | Imran | A61B 5/6882 607/40 |
| 2010/0280531 A1* | 11/2010 | Kalpin | A61M 5/14276 606/148 |
| 2011/0172736 A1* | 7/2011 | Gefen | A61N 1/0543 607/54 |
| 2011/0295335 A1* | 12/2011 | Sharma | A61B 5/4211 607/40 |
| 2013/0053941 A1* | 2/2013 | Costello | A61F 2/88 623/1.11 |
| 2016/0220814 A1* | 8/2016 | Chiao | A61N 1/36007 |
| 2017/0361090 A1* | 12/2017 | Gifford, III | A61N 1/0507 |

OTHER PUBLICATIONS

Office Action dated Jan. 20, 2020, issued in counterpart KR Application No. 10-2018-0047351, with English translation (8 pages).

\* cited by examiner

STIMULATOR FOR DIGESTIVE ORGAN

CROSS-REFERENCE TO RELATED APPLICATION(S)

This application claims the benefit of Korean Patent Application No. 10-2018-0047351, filed on Apr. 24, 2018, in the Korean Intellectual Property Office, the disclosure of which is incorporated herein by reference.

BACKGROUND

1. Field of the Invention

Example embodiments relate to a stimulator for a digestive organ, and more particularly, to a stimulator for a digestive organ that may provide an electrical stimulation when an electrode member is inserted and fixed at a specific location within a digestive organ (for example, an esophagus, a stomach, a large intestine, and the like).

2. Description of the Related Art

Functional gastrointestinal diseases among gastrointestinal diseases are chronic or recurrent diseases that affect about 40% of adults. Although medication or surgery is performed for a treatment of functional gastrointestinal disorders, there are limitations in terms of effects or patient satisfaction. Recently, an electrical stimulation of a gastrointestinal tract is being used to treat functional gastrointestinal diseases.

For example, Korean Patent Publication No. 10-2014-0098780 discloses a "noninvasive neuromodulation device for enabling recovery of motor, sensory, autonomic, sexual, vasomotor and cognitive function."

The above information disclosed in the Background section is possessed or acquired by inventors in a process of achieving the inventive concept, and is not necessarily a technology publicly disclosed before the filing date of this application.

SUMMARY

Example embodiments provide a stimulator for a digestive organ that may provide an electrical stimulation when an electrode member is inserted and fixed at a specific location (for example, a submucous layer or a muscle layer of a gastrointestinal tract) within a digestive organ.

Example embodiments provide a stimulator for a digestive organ that may be accurately located at a specific location within a digestive organ using endoscopic forceps and may be stably fixed at the specific location using an endoscopic clip or an endoscopic suture.

Example embodiments provide a stimulator for a digestive organ that may be minimally invasively inserted into a digestive organ using an endoscope without a need to perform an operation under a general anesthesia.

Example embodiments provide a stimulator for a digestive organ that may be used to treat a functional gastrointestinal disease and also be used for the purposes of, for example, an obesity treatment or a gastrointestinal function rehabilitation treatment of a spinal cord injury patient.

Example embodiments provide a stimulator for a digestive organ that may be configured to semipermanently control a movement of a digestive organ by applying a wireless charging, and that may be further miniaturized to have a compact structure.

According to an aspect, there is provided a stimulator for a digestive organ which includes a case, a substrate member disposed in the case, and an electrode member connected to the substrate member and extending to protrude outwardly from the case, wherein the electrode member has a shape of a wire and is configured to provide an electrical stimulation in a state of being inserted and fixed at a predetermined location within a digestive organ.

At least two ring elements may be provided on an outer surface of the case. The case may be fixed in the digestive organ by an endoscopic clip or an endoscopic suture.

The substrate member may include an upper substrate, and a lower substrate separated from the upper substrate. The electrode member may be connected to the lower substrate in a direction opposite to the upper substrate.

The stimulator may further include a battery member disposed between the upper substrate and the lower substrate and electrically connected to the upper substrate and the lower substrate.

The substrate member may have a cross-sectional shape of "U." The electrode member may be accommodated in an inner space of the substrate member.

An electrical stimulation provided by the electrode member may be controlled by an external control device.

The stimulator may further include a wireless communicator configured to transmit and receive a signal to and from the external control device, and a controller configured to control current flowing in the electrode member based on a signal received by the external control device. The wireless communicator and the controller may be disposed on the upper substrate. The controller may be configured to control on/off, a pulse frequency or a pulse width of the current flowing through the electrode member.

The electrode member may be formed to protrude by a length of 1 mm to 3 mm outwardly from a surface of the case.

The case may have a disc shape.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1:
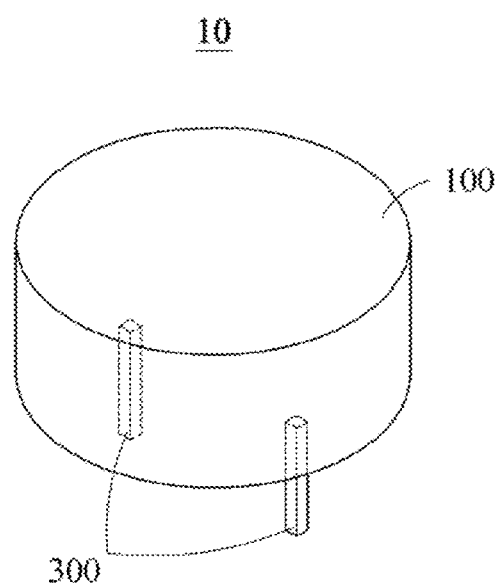
FIG. 1 is a perspective view illustrating a stimulator for a digestive organ according to an example embodiment.

Hereinafter, example embodiments will be described with reference to the accompanying drawings. In the following description, the same elements will be designated by the same reference numerals although they are shown in different drawings. Also, in the following description of example embodiments, a detailed description of known functions and configurations incorporated herein will be omitted when it is deemed that such description will cause ambiguous interpretation of the example embodiments.

Also, to describe components according to example embodiments, the terms first, second, A, B, (a), (b), etc. may be used herein. These terms are merely used to distinguish one component from another, but not to define an essence, order or sequence of the components. It should be noted that if it is described in the specification that one component is "connected", "coupled", or "joined" to another component, it can be directly connected or coupled to the other component, or intervening components may be present.

A component included in one example embodiment and a component having a common function will be described using the same names in other example embodiments. Description of one example embodiment may be applied to other example embodiments, and overlapping detailed descriptions thereof will be omitted, unless mentioned otherwise.

Figure 2:
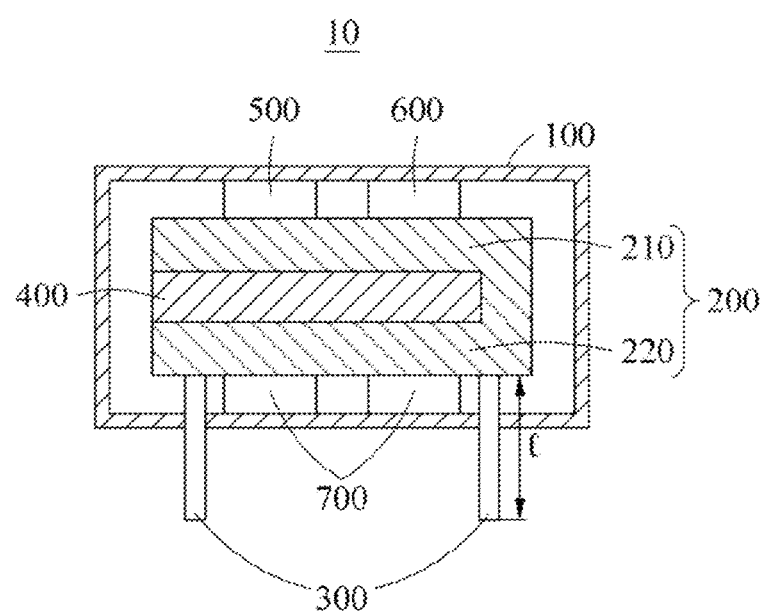
FIG. 2 is a cross-sectional view of a stimulator for a digestive organ according to an example embodiment.
Figure 3:
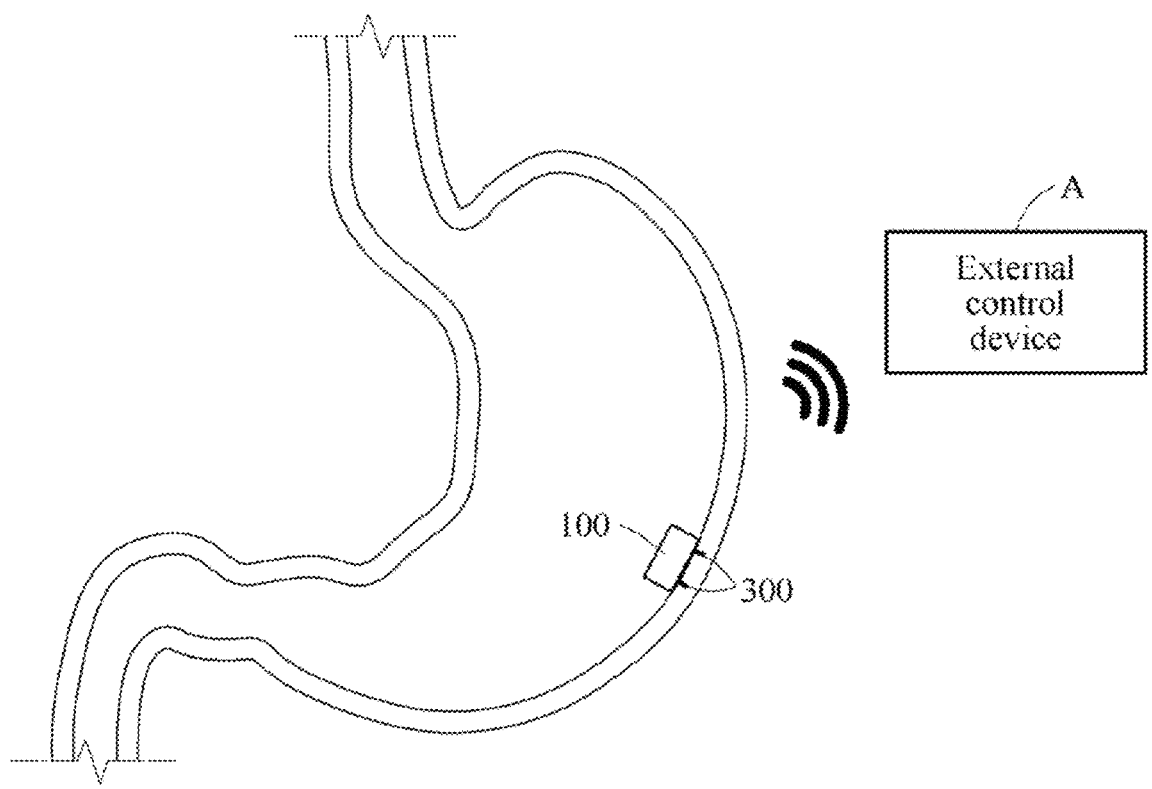
FIG. 3 illustrates an example in which a stimulator for a digestive organ according to an example embodiment is inserted and fixed into a gastrointestinal tract.
Figure 4:
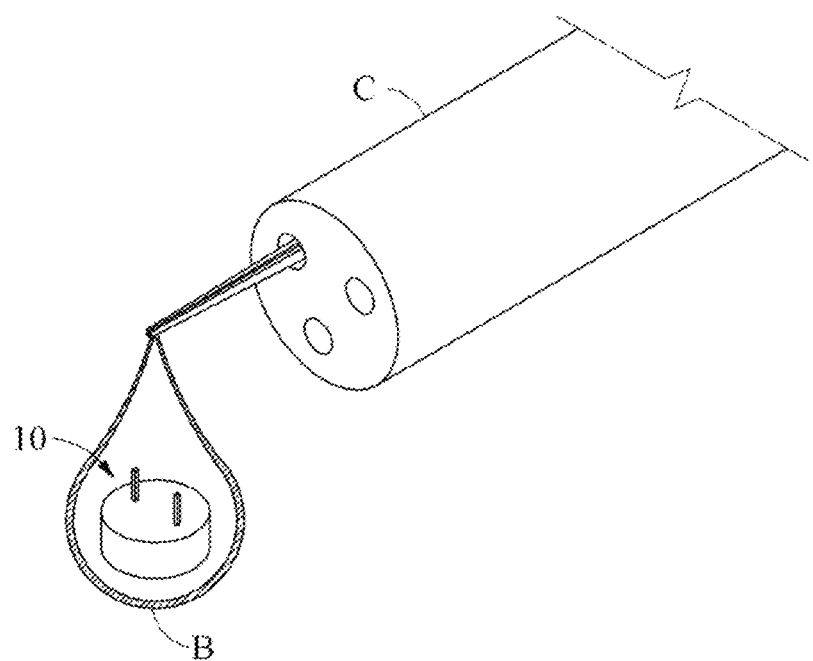
FIG. 4 illustrates an example in which a stimulator for a digestive organ according to an example embodiment is inserted into a rubber pouch and is moved by endoscopic forceps.
Figure 5:
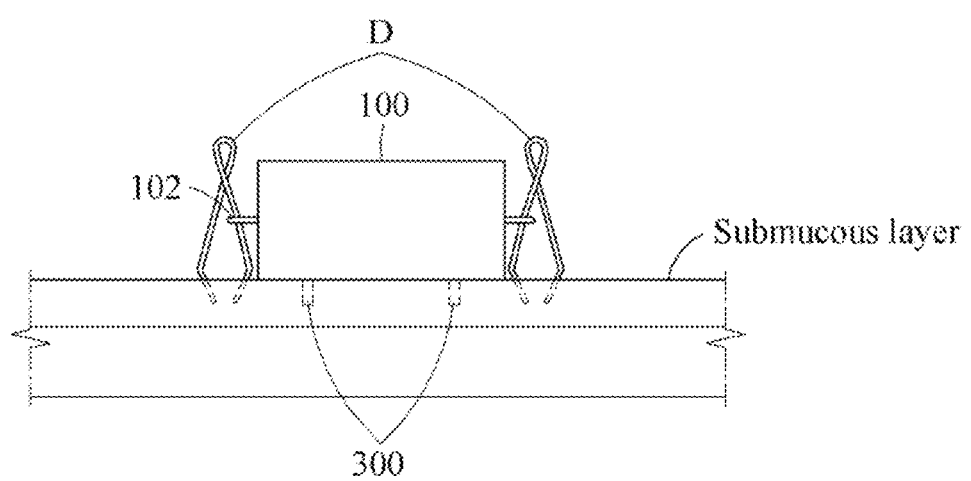
FIG. 5 illustrates an example in which a stimulator for a digestive organ according to an example embodiment is fixed in a gastrointestinal tract by endoscopic clips.
Figure 6:
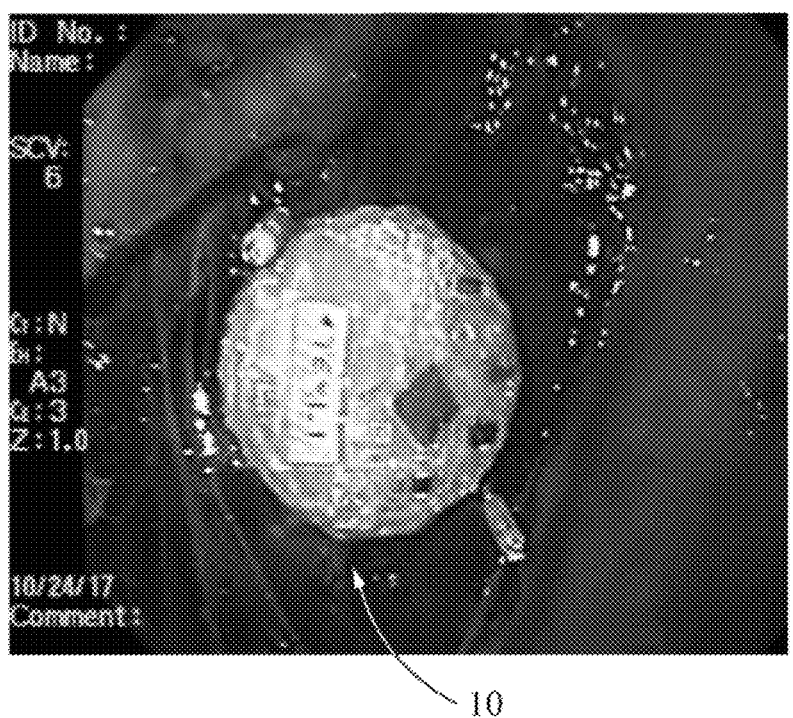
FIG. 6 is a photograph of a stimulator for a digestive organ according to an example embodiment inserted and fixed into a gastrointestinal tract of a pig.

FIG. 1 is a perspective view illustrating a stimulator for a digestive organ according to an example embodiment, and FIG. 2 is a cross-sectional view of a stimulator for a digestive organ according to an example embodiment. FIG. 3 illustrates an example in which a stimulator for a digestive organ according to an example embodiment is inserted and fixed into a gastrointestinal tract, and FIG. 4 illustrates an example in which a stimulator for a digestive organ according to an example embodiment is inserted into a rubber pouch and is moved by endoscopic forceps. FIG. 5 illustrates an example in which a stimulator for a digestive organ according to an example embodiment is fixed in a gastrointestinal tract by endoscopic clips, and FIG. 6 is a photograph of a stimulator for a digestive organ according to an example embodiment inserted and fixed into a gastrointestinal tract of a pig.

Referring to FIGS. 1 through 3, a stimulator 10 for a digestive organ according to an example embodiment may include a case 100, a substrate member 200, an electrode member 300, a battery member 400, a wireless communicator 500, a controller 600 and a lower module 700.

Hereinafter, examples of applying the stimulator 10 to a gastrointestinal tract will be described. For example, the stimulator 10 may be applicable to a digestive organ, for example, an esophagus or a large intestine.

The case 100 may have an inner space to accommodate the substrate member 200, the electrode member 300, the battery member 400, the wireless communicator 500, the controller 600 and the lower module 700.

The case 100 may have a disc shape, however, a shape of the case 100 is not limited thereto. The case 100 may have all structures capable of facilitating an insertion into a gastrointestinal tract.

The case 100 may be formed of silicon or a biocompatible material (or a biomaterial). The case 100 may be formed of another material, and a surface of the case 100 may be coated with silicon or a biocompatible material.

For example, the surface of the case 100 may be coated with silicon using a nano-implant coating technology, or an inert material functional surface may be formed on the surface of the case 100 using a nano-surface modification technology.

Thus, it is possible to prevent a fibrosis, a cytotoxicity or an inflammation from occurring in a submucosal layer of a gastrointestinal tract, and possible to provide insulation and waterproofing.

The case 100 being connected to an endoscope may be orally inserted into the gastrointestinal tract. Thus, a location of the case 100 in the gastrointestinal tract may be verified, and thus the case 100 may be located in a more accurate location and an electrical stimulation may be accurately provided to a specific location within the gastrointestinal tract.

The case 100 may include a connection structure for an endoscope, although not shown in FIGS. 1-3 of the drawings. For example, the case 100 may include a connection element with a shape of a ring or tongs (e.g., see rings 102 in FIG. 5), to fix the case 100 in an end portion of the endoscope.

The substrate member 200 may be located in the case 100.

The substrate member 200 may be a double-sided FR-4 printed circuit board (PCB).

For example, the substrate member 200 may have a cross-sectional shape of "U."

The substrate member 200 may be located so that a top surface of the substrate member 200 may face a top surface of the case 100 and that a bottom surface of the substrate member 200 may face a bottom surface of the case 100. The battery member 400 may be located in an inner space of the substrate member 200.

However, the cross-sectional shape of the substrate member 200 is not limited thereto, and the substrate member 200 may have all cross-sectional shapes that allow the battery member 400 to be connected to the inner space of the substrate member 200.

The substrate member 200 may include an upper substrate 210, and a lower substrate 220 that is separated from the upper substrate 210. The wireless communicator 500 and the controller 600 may be mounted on the upper substrate 210, and the electrode member 300 and the lower module 700 may be mounted on the lower substrate 220. The electrode member 300, the wireless communicator 500, the controller 600 and the lower module 700 will be further described below.

The electrode member 300 may be connected to the substrate member 200 as described above, and connected to the lower substrate 220 in particular.

The electrode member 300 may be formed of a stable conductive material with a relatively high electrical conductivity, for example, copper, platinum, silver or stainless steel.

The electrode member 300 may have a shape of an elongated wire, and may provide an electrical stimulation to a submucous layer or a muscle layer of a gastrointestinal tract in a state of being inserted and fixed at a specific location within the gastrointestinal tract.

Although two electrode members 300 with a shape of wires are shown in FIG. 1 or 2, the number of electrode members 300 is not limited thereto. All electrode members capable of effectively providing an electrical stimulation to a gastrointestinal tract may be used.

For example, the electrode member 300 may be connected to the lower substrate 220 in a form of a through-hole with a dual in-line package (DIP), and may extend to protrude outwardly through a bottom surface of the case 100. In other words, the electrode member 300 may be connected to the lower substrate 220 in an opposite direction to the upper substrate 210.

In this example, a length l of the electrode member 300 may be a sum of a distance between the lower substrate 220 and the bottom surface of the case 100, a thickness of the case 100 and a length of a protruding portion of the electrode member 300.

The protruding portion of the electrode member 300 may have a length suitable to be stably inserted and fixed into a gastrointestinal tract, and may have a length of 1 mm to 3 mm based on a thickness of a muscle layer or a submucous layer of a gastrointestinal tract.

In particular, referring to FIG. 3, the above-described electrode member 300 may be inserted and fixed into a muscle layer or a submucous layer of a gastrointestinal tract. For example, the protruding portion of the electrode member 300 may be inserted into the submucosal layer or the muscle layer of the gastrointestinal tract and the bottom surface of the case 100 may come into contact with an inner wall of the gastrointestinal tract.

Referring to FIG. 4, the stimulator 10 being inserted into a rubber pouch B formed of rubber may be inserted into a gastrointestinal tract using endoscopic forceps C. As shown in FIG. 5, the case 100 may be fixed by endoscopic clips D, to more reliably maintain a state in which the electrode member 300 is inserted and fixed into a muscle layer or a submucous layer of a gastrointestinal tract. Thus, it is possible to prevent the electrode member 300 from being separated from the muscle layer or the submucous layer of the gastrointestinal tract due to a movement of the gastrointestinal tract.

Also, a ring element 102 fixed by the endoscopic clip D may be provided on an outer surface of the case 100. For example, at least two ring elements 102 may be provided.

Although FIG. 5 illustrates an example in which the case 100 is fixed by the endoscopic clips D, the case 100 may also be fixed by an endoscopic suture.

In an example, when the stimulator 10 inserted into the rubber pouch B is connected to the endoscopic forceps C and is orally inserted into a gastrointestinal tract, the stimulator 10 may be discharged from the rubber pouch B and the electrode member 300 may be inserted at a specific location within the gastrointestinal tract. An endoscopic clip tool or an endoscopic suturing tool may be orally inserted into the gastrointestinal tract, and the case 100 may be fixed by the endoscopic clips D or the endoscopic suture.

In another example, in the stimulator 10 inserted into the rubber pouch B, the endoscopic clips D may be mounted already by the ring element 102 of the case 100. In this example, when the stimulator 10 is discharged from the rubber pouch B, the endoscopic clips D may be inserted and fixed at a specific location within the gastrointestinal tract by the endoscopic forceps C.

To insert and fix the stimulator 10 as described above, all schemes of fixing the case 100 at a specific location within a gastrointestinal tract to prevent the electrode member 300 from being separated from a muscle layer or a submucous layer of the gastrointestinal tract may be used.

As described above, the battery member 400 may be located in the inner space of the substrate member 200, for example, between the upper substrate 210 and the lower substrate 220.

The battery member 400 may be electrically connected to the upper substrate 210 and the lower substrate 220. For example, a negative electrode of the battery member 400 may be in contact with the upper substrate 210, and a positive electrode of the battery member 400 may be in contact with the lower substrate 220.

The battery member 400 may include, for example, a lithium rechargeable battery. For example, when the case 100 is removed, the battery member 400 may be charged within the substrate member 200 by a wireless charging technology.

For example, current may flow in the electrode member 300 in response to a power supply from the battery member 400, and an electrical stimulation may be provided to a submucous layer or a muscle layer of a gastrointestinal tract.

In this example, the provided electrical stimulation may be controlled by an external control device A.

The external control device A may include a microprocessor and a display, and an operation of the stimulator 10 may be controlled via a wireless communication with the stimulator 10. The external control device A may include, for example, all external control devices capable of displaying a state of the stimulator 10.

For example, the wireless communicator 500 disposed on the upper substrate 210 may transmit and receive a signal to and from the external control device A. The controller 600 disposed on the upper substrate 210 may control current flowing in the electrode member 300 based on a signal received from the external control device A.

In this example, the wireless communicator 500 may include a radio frequency (RF) transceiver and may be utilized for wireless charging of the battery member 400, however, a configuration of the wireless communicator 500 is not limited thereto. The wireless communicator 500 may include, for example, all communicators capable of performing a wireless communication with the external control device A and wirelessly charging the battery member 400.

For example, the wireless communicator 500 may receive, from the external control device A, a control signal for on/off, a pulse frequency, a pulse width, or on/off time values of current flowing through the electrode member 300, and may transmit, to the external control device A, a signal for an amount of power remaining in a battery or a state value of a submucous layer or a muscle layer of a gastrointestinal tract detected from the electrode member 300.

Also, the control signal transmitted to the wireless communicator 500 may be transferred to the controller 600, to control the on/off, the pulse frequency, the pulse width, or the on/off time values of the current flowing through the electrode member 300. For example, the controller 600 may function to control a variable associated with a flow of current in an electric circuit formed by the substrate member 200, the electrode member 300 and the battery member 400.

For example, the controller 600 may control a frequency, an amplitude, a pulse width, an on time and an off time of current flowing through the electrode member 300 to be 14 Hz, 5 mA, 330 microseconds, an amount of time between 0.1 seconds to 1.0 seconds, and an amount of time between 5.0 seconds to 4.0 seconds, respectively.

The lower module 700 mounted on the lower substrate 220 may be separated from a submucous layer of a gastrointestinal tract so that the case 100 may be interposed therebetween. Also, the lower module 700 may function as an outputter that is in contact with a skin through the electrode member 300. Thus, the lower module 700 may function to control a variable associated with a flow of current in an electric circuit formed by the substrate member 200, the electrode member 300 and the battery member 400, similarly to the controller 600, or may function to maintain a shape of the case 100.

As described above, when the electrode member 300 is inserted and fixed at a specific location within a gastrointestinal tract, the stimulator 10 may provide an electrical stimulation, and may semipermanently control a movement of the gastrointestinal tract by applying a wireless charging or a wireless communication. In addition, the stimulator 10 may be used to treat a functional gastrointestinal disease and also be used for the purposes of, for example, an obesity treatment or a gastrointestinal function rehabilitation treatment of a spinal cord injury patient.

According to example embodiments, a stimulator for a digestive organ may provide an electrical stimulation when an electrode member is inserted and fixed at a specific location (for example, a submucous layer or a muscle layer of a gastrointestinal tract) within a digestive organ.

According to example embodiments, a stimulator for a digestive organ may be accurately located at a specific location within a digestive organ using endoscopic forceps and may be stably fixed at the specific location using an endoscopic clip or an endoscopic suture.

According to example embodiments, a stimulator for a digestive organ may be minimally invasively inserted into a digestive organ using an endoscope without a need to perform an operation under a general anesthesia.

According to example embodiments, a stimulator for a digestive organ may be used to treat a functional gastrointestinal disease and also be used for the purposes of, for example, an obesity treatment or a gastrointestinal function rehabilitation treatment of a spinal cord injury patient.

According to example embodiments, a stimulator for a digestive organ may be used to semipermanently control a movement of a digestive organ by applying a wireless charging, and may be further miniaturized to have a compact structure.

While this disclosure includes specific example embodiments, it will be apparent to one of ordinary skill in the art that various changes in form and details may be made in these example embodiments without departing from the spirit and scope of the claims and their equivalents. The example embodiments described herein are to be considered in a descriptive sense only, and not for purposes of limitation. Descriptions of features or aspects in each example embodiment are to be considered as being applicable to similar features or aspects in other example embodiments. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A stimulator for a digestive organ, the stimulator comprising:
   a case;
   a substrate member disposed in the case; and
   an electrode member connected to the substrate member and extending outwardly from the substrate member to and through a wall of the case and protruding outwardly from the case;
   wherein the electrode member has a shape of an elongated wire, the electrode member is formed to protrude by a length of 1 mm to 3 mm outwardly from a bottom surface of the case, and the electrode member is configured to penetrate into a layer of a digestive organ with said bottom surface resting upon a surface of the digestive organ;
   wherein the electrode member is configured to provide an electrical stimulation in a state of being inserted and fixed at a predetermined location within the digestive organ, said stimulator including at least one fixing element for fixing the stimulator at the predetermined location within the digestive organ,
   wherein the substrate member comprises:
   an upper substrate; and
   a lower substrate having a region separated from the upper substrate, and
   wherein the electrode member is connected to the lower substrate at a side of the lower substrate opposite to the upper substrate, so that said stimulator is minimally invasively insertable into a digestive organ using an endoscope, and
   the stimulator further comprising:
   a battery member disposed between the upper substrate and the lower substrate and electrically connected to the upper substrate and the lower substrate.

2. The stimulator of claim 1, wherein at least two ring elements are provided on an outer surface of the case, and wherein the case is fixed in the digestive organ by an endoscopic clip or an endoscopic suture.

3. The stimulator of claim 1, wherein the substrate member has a cross-sectional shape of "U," and the electrode member is accommodated in an inner space of the substrate member.

4. The stimulator of claim 1, wherein an electrical stimulation provided by the electrode member is controlled by an external control device.

5. The stimulator of claim 4, further comprising:
   a wireless communicator configured to transmit and receive a signal to and from the external control device; and
   a controller configured to control current flowing in the electrode member based on a signal received by the external control device,
   wherein the wireless communicator and the controller are disposed on the upper substrate, and
   wherein the controller is configured to control on/off, a pulse frequency or a pulse width of the current flowing through the electrode member.

6. The stimulator of claim 1, wherein the case has a disc shape.

7. The stimulator of claim 1, wherein the case includes an endoscope connector for connection to an endoscope.

8. The stimulator of claim 7, wherein said endoscope connector includes a connection element with a shape of a ring or tongs.

9. The stimulator of claim 1, wherein the bottom surface is disc shaped.

10. The stimulator of claim 9, wherein the case has a disc shape.

11. The stimulator of claim 1, further including at least one additional electrode member formed to protrude from said bottom surface parallel to said electrode member.

12. The stimulator of claim 5, wherein the wireless communicator and the controller are disposed on an outer side of the upper substrate that faces away from lower substrate.

* * * * *